United States Patent [19]
Sato et al.

[11] Patent Number: 5,196,560
[45] Date of Patent: Mar. 23, 1993

[54] PROCESS FOR PREPARING FLUORINE-CONTAINING DIMETHYLCHLOROSILANES

[75] Inventors: Shinichi Sato; Hitoshi Kinami; Takashi Matsuda; Hirokazu Yamada, all of Annaka, Japan

[73] Assignee: Shin-Etsu Chemical Co., Ltd., Tokyo, Japan

[21] Appl. No.: 720,705

[22] Filed: Jun. 25, 1991

[30] Foreign Application Priority Data

Jun. 26, 1990 [JP] Japan ................................. 2-168038

[51] Int. Cl.$^5$ .............................................. C07F 7/08
[52] U.S. Cl. ................................................... 556/479
[58] Field of Search ......................................... 556/479

[56] References Cited

U.S. PATENT DOCUMENTS

| | | | |
|---|---|---|---|
| 4,658,049 | 4/1987 | Nakano et al. | 556/437 |
| 5,017,718 | 5/1991 | Ojima et al. | 556/476 X |
| 5,047,491 | 9/1991 | Saho et al. | 556/479 X |

Primary Examiner—Arthur C. Prescott
Attorney, Agent, or Firm—Oblon, Spivak, McClelland, Maier & Neustadt

[57] ABSTRACT

Fluorine-containing dimethylchlorosilanes are prepared by reacting an ethylene compound having a fluorine-containing organic group with dimethylchlorosilane in the presence of a rhodium complex, for instance RhCl(PPh$_3$) (Ph: phenyl group), as a catalyst. The use of a rhodium complex as a catalyst enables preparation in high yield of the fluorine-containing dimethylchlorosilane, which has been heretofore obtainable only in low yields.

7 Claims, No Drawings

PROCESS FOR PREPARING FLUORINE-CONTAINING DIMETHYLCHLOROSILANES

BACKGROUND OF THE INVENTION

1. Field of the Invention

This invention relates to a process for preparing fluorine-containing dimethylchlorosilanes in high yields by a reaction between an ethylene compound having a fluorine-containing organic group and dimethylchlorosilane.

2. Description of the Prior Art

It is well known that fluorine-containing dimethylchlorosilanes can be obtained by reacting a fluorine-containing alkylethylene with dimethylchlorosilane. This reaction is represented by the following reaction formula:

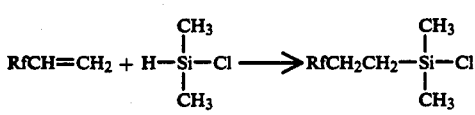

wherein Rf is a fluorine-containing organic.

Conventionally, the above reaction has been carried out using a platinum complex or a peroxide as a catalyst. The conventional method has the problem that the desired product can be obtained only in low yield.

SUMMARY OF THE INVENTION

Accordingly it is an object of this invention to provide a process for preparing fluorine-containing dimethylchlorosilanes in high yields by a reaction of an ethylene compound having a fluorine-containing organic group, such as a fluorine-containing alkylethylene, with dimethylchlorosilane.

According to this invention, there is provided a process for preparing a fluorine-containing dimethylchlorosilane, which comprises reacting an ethylene compound having a fluorine-containing organic group with dimethylchlorosilane in the presence of a rhodium complex.

By the use of a rhodium complex as a reaction catalyst, it has become possible to obtain fluorine-containing dimethylchlorosilanes in shorter time and in higher yield, as compared with the conventional processes.

DETAILED DESCRIPTION OF THE INVENTION

Ethylene compound

The ethylene compound used as a starting material in this invention has, for example, the following formula:

$$Rf-CH=CH_2$$

Wherein Rf is a monovalent fluorine-containing organic group, or $$CH_2=CH-Rf'-CH=CH_2$$

wherein Rf' is a divalent fluorine-containing organic group.

The monovalent fluorine-containing organic group Rf includes, for example, perfluoroalkyl groups having the formula:

$$C_lF_{2l+1}-$$

wherein l is an integer of 1 or above, preferably from 1 to 10, perfluoroalkyl ether groups having the formula:

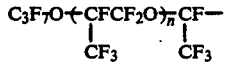

wherein n is an integer of 0 or above, preferably from 0 to 10, and groups which are derived from these groups by substitution of hydrogen atoms for part of the fluorine atoms in these group.

The divalent fluorine-containing organic groups Rf' includes, for example, perfluoroalkylene groups having the formula:

$$-C_mF_{2m}-$$

wherein m is an integer of 1 or above, preferably from 1 to 10, perfluoroalkylene ether groups having the formula:

wherein p and q are integers of 0 or above, preferably such integers that p+q is from 0 to 10, and groups which are derived from these groups by substitution of hydrogen atoms for part of the fluorine atoms in these groups.

Of the ethylene compounds having the monovalent or divalent fluorine-containing organic group as mentioned above, those which are particularly preferred for use in this invention include the followings:

$$CF_3CH=CH_2, C_2F_5CH=CH_2, C_3F_7CH=CH_2,$$

$$C_4F_9CH=CH_2, C_6F_{13}CH=CH_2, C_8F_{17}CH=CH_2,$$

$$CH_2=CHC_6F_{12}CH=CH_2,$$

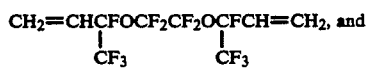

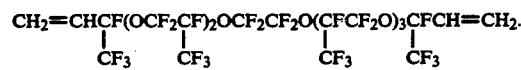

Rhodium complex

Preferable examples of the rhodium complex to be used as a reaction catalyst in the process of this invention include RhCl(PPh₃)₃, RhCl(CO)(PPh₃)₂, [Rh(CH₃COO)₂]₂, [RhCl(C₂H₄)₂]₂, [RhCl(C₇H₈)]₂ (wherein C₇H₈ is norbornadiene as a divalent ligand), Rh(CH₃COCHCOCH₃)₃, etc. In the above formulas, and hereinafter, Ph stands for the phenyl group.

The rhodium complexes are used preferably in an amount of from $1.0\times10^{-8}$ to $1.0\times10^{-1}$ mole, more preferably from $1.0\times10^{-6}$ to $1.0\times10^{31\ 3}$ mole, per mole of the ethylene compound.

Reaction

The reaction between the ethylene compound having a fluorine-containing organic group and dimethylchlorosilane is carried out in the presence of the rhodium complex at a pressure of preferably 2 atm or above, more preferably from 4 to 10 atm, and a temperature of from 50° to 250° C., preferably from 70° to 150° C. The reaction under these conditions is carried out, for example, in an autoclave.

In carrying out the reaction, it is generally desirable to use dimethylchlorosilane in an amount of from 1.0 to 5.0 moles, preferably from 1.1 to 2.0 moles, per mole of an ethylenic double bond contained in the ethylene compound.

The reaction proceeds according to the aforementioned reaction formula. For example, when the ethylene compound used is a monofunctional one, a fluorine-containing dimethylchlorosilane having the following general formula [I]:

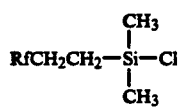

wherein Rf is a monovalent fluorine-containing organic group, is obtained in a high yield. The fluorine-containing dimethylchlorosilane thus obtained is useful as a silylating agent, a silica treating agent, a raw material for surfactants, etc.

When a bifunctional ethylene compound is used, on the other hand, the aforementioned reaction produces a dimethylchlorosilane having the following general formula [II]:

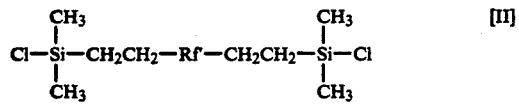

wherein Rf' is a divalent fluorine-containing organic group. This dimethylchlorosilane is useful as a raw material for hybrid silicones having a fluorine-modified backbone.

EXAMPLES

Example 1

A 300-ml autoclave equipped with a stirrer and a thermometer was charged with 179 g of n-$C_4F_9CH=CH_2$, 98 g of dimethylchlorosilane and 0.11 g of $RhCl(PPh_3)_3$ (Wilkinson's complex), and the resultant mixture was stirred with heating at 100° C. under a pressure of 7 atm for 4 hours.

After the reaction, the reaction product was cooled to 25° C. and taken out of the autoclave. A quantitative analysis of the reaction product by gas chromatography gave a conversion of n-$C_4F_9CH=CH_2$ of 93% and a selectivity of 93% for dimethylchlorosilane having the following formula:

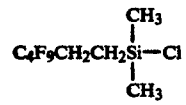

Example 2

The same 300-ml autoclave as that used in Example 1 was charged with 177 g of $CH_2=CHC_6F_{12}CH=CH_2$, 122 g of dimethylchlorosilane and 0.08 g of $RhCl(PPh_3)_3$, and the resultant mixture was stirred with heating at 110° C. and 8 atm for 6 hours.

After the reaction, the reaction product was quantitatively analyzed in the same manner as in Example 1. The analysis gave a conversion of $CH_2=CHC_6F_{12}CH=CH_2$ of 99% and a selectivity of 79% for the addition reaction product having the following formula:

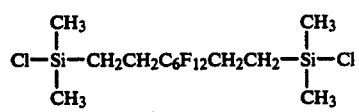

Example 3

The same 300-ml autoclave as that used in Example 1 was charged with 239 g of

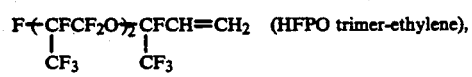

61 g of dimethylchlorosilane and 0.09 g of $RhCl(PPh_3)_3$, and the resulting mixture was stirred with heating at 100° C. and 6 atm for 6 hours.

After the reaction, the reaction product was analyzed quantitatively in the same manner as in Example 1. The conversion of the HFPO trimer-ethylene was 86%, and the selectivity for the addition product having the following formula:

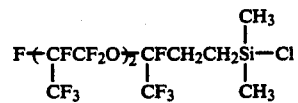

was 88%.

Examples 4–7

Reactions were carried out in the same manner as in Example 1 except that 0.1 g each of other rhodium catalysts were used in place of $RhCl(PPh_3)_3$. The results are shown in Table 1 below.

TABLE 1

| Example | Catalyst | Conversion (%) | Selectivity (%) |
|---|---|---|---|
| 4 | [Rh(CH$_3$COO)$_2$]$_2$ | 87 | 89 |
| 5 | RhCl(CO)(PPH$_3$)$_2$ | 88 | 92 |
| 6 | [RhCl(C$_2$H$_4$)$_2$]$_2$ | 81 | 90 |
| 7 | Rh(CH$_3$COCHCOCH$_3$)$_3$ | 82 | 87 |

Comparative Examples 1–8

Reactions were carried out in the same manner as in Example 1 except that various catalysts were used in place of $RhCl(PPh_3)_3$. The results, such as the selectivity for the desired addition product, are shown in Table 2 below.

TABLE 2

| Comparative Example | Catalyst | Amount of catalyst (g) | Conversion (%) | Selectivity (%) |
|---|---|---|---|---|
| 1 | H$_2$PtCl$_6$.6H$_2$O | 0.1 | 66 | 93 |
| 2 | (t-BuO—)$_2$— | 1.2 | 52 | 89 |
| 3 | PdCl$_2$(PPh$_3$)$_2$ | 0.1 | 44 | 91 |
| 4 | PtCl$_2$(PPh$_3$)$_2$ | 0.1 | 5 | 94 |

TABLE 2-continued

| Comparative Example | Catalyst | Amount of catalyst (g) | Conversion (%) | Selectivity (%) |
|---|---|---|---|---|
| 5 | Mo(Co)$_6$ | 0.06 | 36 | 88 |
| 6 | IrCl(CO)(PPh$_3$)$_2$ | 0.1 | 12 | 95 |
| 7 | Ru$_3$(CO)$_{12}$ | 0.1 | 19 | 90 |
| 8 | RuCl$_2$(PPh$_3$)$_3$ | 0.1 | 7 | 92 |

We claim:

1. A process for preparing a fluorine-containing dimethylchlorosilane, which comprises reacting an ethylene compound having a fluorine-containing organic group with dimethylchlorosilane in the presence of a rhodium complex.

2. The process according to claim 1, wherein the rhodium complex comprises at least one compound selected from the group consisting of RhCl(PPh$_3$)$_3$, RhCl(CO)(PPh$_3$)$_2$, [Rh(CH$_3$COO)$_2$]$_2$, [RhCl(C$_2$H$_4$)$_2$]$_2$, [RhCl(C$_7$H$_8$)]$_2$ where C$_7$H$_8$ is norbornadiene as a divalent ligand, and Rh(CH$_3$COCHCOCH$_3$), wherein Ph stands for the phenyl group.

3. The process according to claim 1, wherein the rhodium complex is present in an amount of from $1.0 \times 10^{-8}$ to $1.0 \times 10^{-1}$ mole per mole of the ethylene compound.

4. The process according to claim 1, wherein the reaction is carried out at a pressure of 2 atm or above and a temperature of from 50° to 250° C.

5. The process according to claim 1, wherein the ethylene compound has the following formula:

$$Rf-CH=CH_2$$

or $$CH_2=CH-Rf'-CH=CH_2$$

wherein, in the formulas, Rf is a monovalent fluorine-containing organic group, and Rf' is a divalent fluorine-containing organic group.

6. The process according to claim 5, wherein the group Rf is a perfluoroalkyl group having the formula:

$$C_lF_{2l+1}-$$

wherein l is an integer of 1 or above, or a perfluoroalkyl ether group having the formula:

$$C_3F_7O{\displaystyle \left(CFCF_2O\right)_{\overline{n}}}\underset{CF_3}{\underset{|}{CF}}-$$
$$\phantom{C_3F_7O(}\underset{CF_3}{\underset{|}{\phantom{CF}}}$$

wherein n is an integer of 0 or above.

7. The process according to claim 5, wherein the group Rf' is a perfluoroalkylene group having the formula:

$$-C_mF_{2m}-$$

wherein m is an integer of 1 or above, or a perfluoroalkylene ether group having the formula:

$$-\underset{CF_3}{\underset{|}{CF}}(OCF_2CF)_{\overline{p}}OCF_2CF_2O(CFCF_2O)_{\overline{q}}\underset{CF_3}{\underset{|}{CF}}-$$

wherein p and q are each an integer of 0 or above.

* * * * *